United States Patent [19]

Garrity et al.

[11] Patent Number: 5,019,593

[45] Date of Patent: May 28, 1991

[54] ANTIFUNGAL FERMENTATION PRODUCTS AND COMPOSITIONS THEREOF

[75] Inventors: George M. Garrity, Westfield; Maria B. Lopez, Hillside; Otto D. Hensens, Red Bank; Richard L. Monaghan, Somerset; Deborah L. Zink, Manalapan, all of N.J.

[73] Assignee: Merck & Co., Inc., Rahway, N.J.

[21] Appl. No.: 79,192

[22] Filed: Jul. 29, 1987

[51] Int. Cl.$^5$ .................... A01N 47/42; A01N 37/44; C07C 237/16; C07C 229/30

[52] U.S. Cl. .................................. 514/560; 260/404; 260/404.5; 435/128; 435/129

[58] Field of Search .................. 260/404, 404.5 G; 514/560; 435/128, 129

[56] References Cited

PUBLICATIONS

Mukhopadhyay et al, The Journal of Antibiotics, vol. XL, No. 7 (Jul. 1987), pp. 1050-1052.

Torzybski et al, Antibiotics, vol. III (1978), pp. 2014, 2067 and 2068.

*Primary Examiner*—Richard L. Raymond
*Attorney, Agent, or Firm*—Alice O. Robertson; Hesna J. Pfeiffer

[57] ABSTRACT

A mixture of derivatives of 2-amino-3,4,5,14-tetrahydroxy-6-eicosenoic acid has been isolated from a culture medium after cultivation of microorganisms belonging to the genus Aspergillus. The compounds are useful as antifungal agents.

11 Claims, 4 Drawing Sheets

ANTIFUNGAL FERMENTATION PRODUCTS AND COMPOSITIONS THEREOF

The present invention is concerned with antifungal agents produced by fermentation of the species Aspergillus isolated from soil. The materials show broad antifungal spectrum with especially good activity against *Candida albicans* and *Cryptococcus neoformans*. The invention is also concerned with antifungal compositions containing these agents, their use and their production.

DESCRIPTION OF THE INVENTION

In accordance with the present invention, a fermentation product which is a mixture of 2 amino-3,4,5,14-tetrahydroxy-6 eicosenoic acid and derivatives thereof is produced by fermentation when a previously undescribed strain of Aspergillus, isolated from soil, is grown under controlled conditions.

The antifungal agent produced by the fermentation of said fungus has been determined to be a mixture of four eicosenoic acid compounds which may be represented generically by the formula where R is —H or —COCH$_3$, X is —OH or —O$^\ominus$, Y is or —NH$_3^\oplus$, —NHCOCH$_3$ provided that when R is —H and X is —OH, Y may be —NHCOCH$_3$ or and when R is —H or —COCH$_3$ and X is —O$^\ominus$, Y is —NH$_3^\oplus$.

The four components are represented by the following structures:

(1) 2-quanidino 3,4,5,14-tetrahydroxy-6-eicosenoic acid represented by the formula

(2) 2 amino 3,4,5,14-tetrahydroxy-6-eicosenoic acid represented by the formula (3) 5-acetyloxy-2-amino-3,4,14-trihydroxy-6-eicosenoic acid represented by the formula (4) 2-(acetylamino)-3,4,5,14-tetrahydroxy-6-eicosenoic acid represented by the formula The structures of the component compounds of the antifungal agent of the present invention have been determined by detailed analyses of the various spectral characteristics of the compounds, in particular their nuclear magnetic resonance, mass, ultraviolet and infrared spectra as hereinafter detailed.

The high resolution mass spectral (HRMS) data were obtained on the trimethylsilyl derivatives of each of the components. The derivatives were prepared by treating each component with bis(trimethylsilyl)-trifluoroacetamide (BTSFA), 10:1 (v/v) in pyridine under nitrogen at room temperature for 18 hours. Analogous silylation with perdeutero-BTSFA allowed unambiguous determination of the number of silyl groups in each molecule. The mass spectral data were as follows:

| Compound | Mass Ion Found | Mass Ion Calcd | Silyl Derivative | Molecular Weight | Molecular Formula |
|---|---|---|---|---|---|
| IA | 863.5369 | 863.5367 | M$^+$(C$_3$H$_8$Si)$_6$ | 431 | C$_{21}$H$_{41}$N$_3$O$_6$ |
| IB | 806.4877 | 806.4914 | M$^+$(C$_3$H$_8$Si)$_{5\text{-}1}$ | 389 | C$_{20}$H$_{39}$NO$_6$ |
| IC | 791.4862 | 791.4859 | M$^+$(C$_3$H$_8$Si)$_5$ | 431 | C$_{22}$H$_{41}$NO$_7$ |
| ID | 848.4998 | 848.5020 | M$^+$(C$_3$H$_8$Si)$_{5\text{-}1}$ | 431 | C$_{22}$H$_{41}$NO$_7$ |

The $^1$H NMR spectra of the components are shown in FIGS. 1 to 4 for Component IA, IB, IC and ID, respectively. The spectra were recorded in CD$_3$OD at ambient temperature on a Varian XL-400 NMR spectrometer. Chemical shifts are shown in ppm relative to tetramethylsilane at zero ppm using the solvent peak at Δ3.30 as internal reference.

On the bases of these and other data, the Components IA-ID are believed with a considerable degree of certainty to have the structures indicated.

The compounds are white or light colored solids soluble in polar organic solvents. Thus they are adaptable to be employed in solution. They are also adaptable to be employed in aqueous dispersions.

The compounds of this invention have useful antifungal activities adapted to be employed for the control of various fungi, including those causing pathogenic mycotic infections. The compounds are active against refractory pathogens such as *Candida albicans*. Moreover, in view of substantial lack of toxicity against mammals, the compounds are especially useful in the treatment of fungal diseases. Further, the compounds are useful in other antifungal applications, including treatment of plants and soil, or as sanitizing agents, or as preservatives in the paint, wood, textile, cosmetic, leather, fur, paper and pulp, plastics, fuel, rubber and food industries. In such applications, they may be employed to control the growth of *Aspergillus, Penicillium, Alternaria, Monilia, Aureobasidium* and other fungal species which may be found on or in cosmetics, leather, electrical insulation, textiles, paints and other materials; to control the growth of *Erysiphe polygoni, Alternaria, solani,* and *Cochliobolus miyabeanus* which infect plants, plant parts and plant products; to control *Rhizoctonia solani, Fusarium solani* and *Pythium ultimum* which infect soil; and to control *Lenzites trabea* and *Ceratocytis pilifera* in wood, pulp and paper.

Some other of the specific fungi and yeasts which may be controlled include in *Aspergillus* species: *A. niger, A. flavus, A. fumigatus, A. oryzae, A. awalmari, A. versicolor, A. sydowi. A. nidulans,* and *A. terreus;* or *Penicillium* species: *P. notatum, P. roqueforti, P. chrysogenum, P. oxalicum, P. spinulosum, P. martensii, P. citrinum, P. digitatum, P. expansum, P. italicum, P. cyclopium,* and *P. funiculosum; Neurospora sitophila; Phoma terrestris; Rhizomucor miehei; Alternaria solani, Chaetomium globosum; Trichoderma harzianum; Fusarium oxysporum; Ustilago maydis, Ceratocystis ulmi; Verticillium serrae; Botrytis allii; Saccharomyces cerevisiae; Candida* species such as *C. albicans, C. tropicalis, C. rugosa, C. guilliermondi, C. pseudotropicalis, Torulopsis glabrata,* and *Cryptococcus neoformans.*

The compounds of the invention are conveniently produced by the fermentation of previously unknown strains of the microorganism *Aspergillus fumigatus* designated MF 5013 and MF 5038 in the culture collection of Merck & Co., Rahway, N.J. and recovering said compound from the culture broth. A sample of the cultures, capable of producing the compounds has been deposited under the Budapest Treaty without restriction as to availability in the culture collection of the American Type Culture Collection at 12301 Parklawn Drive, Rockville, MD 20852. The samples have been assigned the accession Nos. ATCC 20859 and ATCC 20857, respectively.

The morphological and cultural characteristics of MF 5013 are set forth below:

A. Morphological characteristics

1. Conidial heads erect, compact and columnar, olive green in color, darkening with age.
2. Vesicles are flask-shaped, smooth, dark olive-green in color, especially in upper part.
3. Sterigmata are in one series, also pigmented and present mostly on upper half.
4. Conidia are globose, echinulate to roughened, dark olive-green in mass, 2.3–3.0 microns in diameter.
5. No perithecia or sclerotia were observed.

B. Cultural characteristics

1. Potato dextrose agar Colonies are white at first, becoming green as conidia develop and becoming dark green to almost black as colonies age. Colonies are rapid growing, spreading and become flocculent. Reverse is yellowish brown, darkening as culture ages. Conidial structures more abundant than on Czapek Dox or Sabouraud maltose agars. Growth is good at 28° C. and 37° C., very poor at 42° C.
2. Czapek Dox agar Colonies are spreading, velvety, cream colored with brownish areas. Reverse is yellowish brown. Conidial structures very few.
3. Sabouraud Maltose agar Colonies are spreading, velvety, white becoming cream-colored with light brown areas. Reverse is yellowish brown. Conidial structures very few.

The morphological and cultural characteristics of MF 5038 are set forth below:

A. Morphological characteristics

1. Conidial heads erect, compact and columnar, olive-green in color, darkening with age.
2. Vesicles are flask shaped, smooth, dark olive green in color, especially in upper part.
3. Sterigmata are in one series, also pigmented and present mostly on upper half.
4. Conidia are globose, echinulate to roughened, dark olive-green in mass, 2.3–3.0 microns in diameter.
5. No perithecia or sclerotia were observed.

B. Cultural characteristics

1. Potato dextrose agar Colonies are white at first, becoming green as conidia develop and becoming dark green to almost black as colonies age. Colonies are rapid growing, spreading and become flocculent. Reverse is yellowish brown, darkening as culture ages. Conidial structures more abundant than on Czapek Dox or Sabouraud maltose agars. Growth is good at 28° C. and 37° C., very poor at 42° C.
2. Czapek Dox agar Colonies are spreading, velvety, cream colored with brownish areas. Reverse is yellowish brown. Conidial structures very few.
3. Sabouraud Maltose agar Colonies are spreading, velvety, white becoming cream colored with light brown areas. Reverse is yellowish brown. Conidial structures very few.

A careful comparison of the foregoing data with published descriptions in "The Genus Aspergillus" by K. A. Raper and D I. Fennell, 1977, Robert E. Krieger Publishing Company, Huntington, N.Y. indicates that the organism can be identified as *Aspergillus fumigatus.* It was therefore determined that MF5013 and MF 5038 are cultures of a new strain of the known species.

Although the invention is explained hereinbelow principally with respect to the specific strain, it is well known in the art that the properties of microorganisms may be varied naturally and artificially. Thus, all strains of the genus *Aspergillus including varieties and mutants, whether obtained by natural selection, produced by the action of mutating agents such as ionizing radiation or ultraviolet irradiation, or by the action of chemical mutagens such as nitrosoguanidine, are contemplated and usable in this invention.*

The compounds of the present invention are produced during the aerobic fermentation of suitable aqueous nutrient media under conditions described hereinafter, with a producing strain of *Aspergillus fumigatus* MF 5013/MF 5038. Aqueous media such as those used for the production of many antifungal substances are suitable for use in this process for the production of this compound.

Such nutrient media contain sources of carbon and nitrogen assimilable by the microorganism and generally low levels of inorganic salts. In addition, the fermentation media may contain traces of metal necessary for the growth of the micro organisms and production of the desired compound These are usually present in sufficient concentrations in the complex sources of carbon and nitrogen, which may be used as nutrient sources, but can, of course, be added separately to the medium, if desired.

In general, nutrients such as dextrose, sucrose, maltose, glycerol, lactose, dextran, cerelose, corn meal, millet, corn, oat flour, and the like, are suitable sources of assimilable carbon in the nutrient media. The exact quantity of the carbon source which is utilized in the medium will depend, in part, upon the other ingredients in the medium, but it is usually found that an amount of carbohydrate between 0.5 and 90% by weight of the medium is satisfactory. These carbon sources can be used individually or several such carbon sources may be combined in the same medium.

Various nitrogen sources such as yeast hydrolysates, yeast autolysates, yeast cells, tomato paste, soybean meal, casein hydrolysates, yeast extracts, corn steep liquors, distillers solubles, cottonseed meal, meat extract, corn, millet and the like, are readily assimilable by *Aspergillus fumigatus* MF 5013/5038 in the production of the instant compounds. The various sources of nitrogen can be used alone or in combination in amounts ranging from 0.2 to 90% by weight of the medium.

Among the nutrient inorganic salts, which can be incorporated in the culture media are the customary salts capable of yielding sodium, potassium, magnesium, ammonium, calcium, phosphate, sulfate, chloride, carbonate, and like ions. Also included are trace metals such as cobalt, manganese, iron, molybdenum, zinc, cadmium and the like. For the best production of the instant compounds, the addition of calcium carbonate to the production medium is most preferred.

The following are examples of media suitable for growing strains of *Aspergillus fumigatus* MF 5013/5038. It should be noted that the media described hereinbelow and in the Examples are merely illustrative of the wide variety of media, which may be employed, and are not intended to be limiting.

| Medium A | |
|---|---|
| Dextrose | 1.0 g. |
| Soluble starch | 10.0 g. |
| Beef extract | 3.0 g. |
| Yeast autolysate (as ardamine pH available from Yeast Products Inc., Clifton, N.J.) | 5.0 g. |
| NZ Amine-E (casein hydrolysate- available from Humko-Sheffield- Memphis, Tenn) | 5.0 g. |
| $MgSO_4.7H_2O$ | 0.05 g. |
| Phosphate Buffer | 2.0 ml. |
| $CaCO_3$ | 0.5 g. |
| Distilled water | 1000 ml. |
| pH | 7.0–7.2 |
| Phosphate Buffer | |
| $KH_2PO_4$ | 91.0 g. |
| $Na_2HPO_4$ | 95.0 g. |
| Distilled water | 1000 ml. |
| pH | 7.0 |
| Medium B | |
| Tomato paste | 20.0 g. |
| Primary yeast | 10.0 g. |
| Dextran (CPC starch) | 20.0 g. |
| $CoCl_2.6H_2O$ | 0.005 g. |
| Distilled water | 1000 ml. |
| pH | 7.2–7.4 |
| Medium C | |
| Corn meal | 20.0 g. |
| Distillers solubles | 10.0 g. |
| Soybean meal | 15.0 g. |
| Sodium citrate | 4.0 g. |
| $CaCl_2.2H_2O$ | 0.5 g. |
| $MgSO_4.7H_2O$ | 0.1 g. |
| $CoCl_2.6H_2O$ | 0.01 g. |
| $FeSO_4.2H_2O$ | 0.01 g. |
| Polyglycol P2000 (Polypropylene glycol mw 2000) | 2.5 mg. |
| Distilled water | 1000 ml. |
| pH | 6.5 |
| Medium D | |
| Lactose | 20.0 g. |
| Distillers solubles | 15.0 g. |
| Autolyzed yeast (Ardamine pH) | 5.0 g. |
| Distilled water | q.s. to 1000 ml. |
| pH | 7.0 |
| Medium E | |
| Tomato paste | 40.0 g. |
| Oat flour | 10.0 g. |
| Distilled water | 1000 ml. |
| pH | 7.0 |
| Medium F | |
| Corn Steep Liquor | 15.0 g. |
| $(NH_4)_2SO_4$ | 4.0 g. |
| $CaCO_3$ | 6.0 g. |
| Soluble Starch | 20.0 g. |
| Corn meal | 1.0 g. |
| Soybean meal | 4.0 g. |
| Glucose | 5.0 g. |
| $KH_2PO_4$ | 0.3 g. |
| Lard oil | 2.5 g. |
| Distilled water | 1000 ml. |
| pH | 6.7 |
| Medium G | |
| Dextrose | 10.0 g. |
| Asparagine | 1.0 g. |
| $K_2HPO_4$ | 0.1 g. |
| $MgSO_4.7H_2O$ | 0.5 g. |
| Yeast Extract | 0.5 g. |
| Oat Flour | 10.0 g. |
| $CaCO_3$ | 3.0 g. |
| Trace Element Mix | 10.0 g. |
| Distilled water | 1000 ml. |
| Adjust pH to | 7.2 |
| Trace Element Mix | |
| $FeSO_4.7H_2O$ | 1000 mg. |
| $MnSO_4.4H_2O$ | 1000 mg. |
| $CuCl_2.2H_2O$ | 25 mg. |
| $CaCl_2.2H_2O$ | 100 mg. |
| $H_3BO_3$ | 56 mg. |
| $(NH_4)_6MO_4O_{24}.6H_2O$ | 19 mg. |
| $ZnSO_4.7H_2O$ | 200 mg. |
| Distilled water | 1000 ml. |
| Medium H | |
| Medium G | 1000 ml. |
| Oat Flour | 10 g. |
| pH | 7.2 |

For producing the compounds of the present invention, a fermentation broth containing *Aspergillus fumigatus* is prepared by inoculating spores or mycelia of the antibiotic producing organism into a suitable medium and then cultivating under aerobic conditions. Cultivation on a solid medium is also possible but for production in large quantities, cultivation in liquid medium is preferable.

The procedure generally is first to inoculate a preserved source of culture from an agar slant containing nutrient medium into a nutrient seed producing medium and to obtain, preferably through a two step procedure, growth of the organisms which serve as seeds in the production of the antifungal agent.

In this process, a slant section of a preserved culture of MF 5013/5038 is inoculated in an appropriate liquid nutrient seed medium and the flasks incubated with or without agitation at temperatures in the range of from about 25° C. to about 30° C., usually about 28° C. Agitation when employed, may be up to 400 RPM, preferably, about 200 to 220 RPM. The incubation is carried out over a period of from 1 to 10 days. When growth is abundant, usually between 2 and 4 days, the culture growth may be used to inoculate the production medium for the production of the antifungal agent. Preferably however, a second stage fermentation is carried out, inoculating with a portion of the culture growth and then employing similar conditions but generally with a shortened incubation period of about 1 to 2 days. The growth then is employed to inoculate the production medium.

The fermentation production medium inoculated with the culture growth is incubated for 3 to 30 days, usually 7 to 14 days with or without agitation. The fermentation may be conducted at temperatures ranging from about 20° C. to about 40° C. For optimum results, it is most convenient to conduct these fermentations at a temperature in the range of from about 15° C. to about 30° C. Temperatures of about 25° C. are most preferred. The pH of the nutrient medium suitable for producing the instant compounds can vary from about 3.0 to 8.0 with a preferred range of from about 4.0 to 6.0. After the appropriate period for the production of the desired compound or compounds, the latter is recovered from the fermentation broth as hereinafter more fully described.

When the fermentation is to be on a small scale, it is conveniently carried out by placing suitable quantities of nutrient medium in a flask employing known sterile techniques, inoculating the flask with either spores or vegetative cellular growth of *Aspergillus fumigatus* MF 5013/5038, loosely stoppering the flask with cotton and permitting the fermentation to proceed at a constant temperature of about 25° C. on a rotary shaker at from 0 to 300 RPM for about 2 to 21 days.

For larger scale operations, it is preferable to conduct the fermentation in suitable tanks provided with an agitator and a means of aerating the fermentation medium. The nutrient medium is made up in the tank and after sterilization is inoculated with a source of vegetative cellular growth of *Aspergillus fumigatus* MF 5013/5038. The fermentation is allowed to continue for from 7 to 14 days while agitating and/or aerating the nutrient medium at a temperature in the range of from about 20 to 30° C. The degree of aeration is dependent upon several factors such as the size of the fermenter, agitation speed, and the like. Generally, the larger scale fermentations are agitated at about 95 to 300 rpm and about 2 to 20 cubic feet per minute (cfm) of air.

After completion of the fermentation, the active material is recovered from the fermentation medium by separating the material from solid material and thereafter is isolated by one or more chromatographic separations.

When the fermentation medium is broth, the recovery may be carried out in the following manner. The broth is first filtered to remove solid impurities and is then placed on a non ionic adsorbent column to adsorb the active component and to separate the water soluble materials in the effluent. The adsorbed material is then eluted from the column using alcohol water, preferably, methanol water as eluting agent and collected in fractions. Fractions showing activity against *Ustilago maydis* are combined and concentrated under reduced pressure to obtain crude product.

If a solid medium is employed for fermentation, recovery may be carried out in the following manner. The fermentation medium is extracted with a water miscible solvent such as lower alcohols, especially as an aqueous mixture. The aqueous extract is placed on a non ionic adsorbent column to adsorb the active component and to remove the water soluble impurities in the effluent. Thereafter, the adsorbed material is eluted as above-described and the same procedure followed as when the product is produced in a liquid medium.

For the initial fractionation in the recovery step, a non-ionic adsorbent resin, as hereinafter detailed, is employed together with an aqueous-alcoholic solvent mixture as eluting agent. The eluting agent is employed with successively increasing concentrations of alcohol until alcohol alone is employed. A representative and preferred successive solvent compositions for elution are 60/40 and 80/20 methanol/water, and methanol. Subsequently, another chromatographic separation is carried out employing a column with a non-ionic absorbent resin with higher capacity employing alcoholic solutions, including methylene chloride/methanol methanol/water, and methanol for elution. The specific resin and eluting solutions may vary depending on the component desired.

The preferred adsorbents are non-ionic adsorbents. Particularly suitable are cross linked styrene-divinylbenzene copolymers and halogenated styrene divinylbenzene copolymers. The preferred adsorbent for the final purification step is "Sepabeads SP 207," a brominated styrene divinylbenzene copolymer available commercially and manufactured by Mitsubishi Chemical Industries, Ltd. For the initial and intermediate chromatographic separations, styrene divinylbenzene copolymers available commercially as Diaion HP-20, HP-30, HP-40 (Mitsubishi Chemical Industries, Ltd) and Amberlite XAD-2 and XAD-4 (Rohm and Haas Co.) may be employed. Still other adsorbents such as silica gel, alumina, dextran gels and the like also may be employed, but are less preferred.

The novel compounds of the present invention may be recovered from the eluates by combining and concentrating appropriate fractions. If desired, the concentrate or residue may be subjected to conventional purification procedures.

The antifungal activity of the compounds may be detected in an antifungal assay employing disc diffusion methods against a panel of representative yeasts, filamentous fungi (molds) and bacteria.

The filamentous fungi used in the assay are *Cochliobolus miyabeanus, Penicillium* sp. (three strains), *Aspergillus niger, Trichoderma* sp., *Phoma* sp., *Trichoderma lignorum, Fusarium oxysporum, Ustilago maydis, Ceratocystis ulmi, Alternaria solani, Verticillium serrae, Botrytis allii, Scopulariopsis communis, Cephalosporium* sp., *Cer-

*cospora beticola, Saccharomyces cerevisiae, Rhizomucor miehei, Aspergillus flavus* and *Aspergillus fumigatus.*

The yeasts employed in the assay are *Saccharomyces cerevisiae, Candida albicans, Aspergillus niger, Candida tropicalis, Candida rugosa, Brettanomyces bruxellensis, Torulospora hansenii, Candida guilliermondi, Candida pseudotropicalis, Torulopsis glabrata, Cryptococcus albidus,* and *Cryptococcus laurentii.*

The bacteria employed in the assay are *Streptomyces sp., Acholeplasma laidlawii* and *Bacillus subtilis.*

For carrying out the assay, seeded assay plates are prepared in the following manner according to the type of assay strain.

Inocula for filamentous fungi are prepared by scraping the surface of stock plates maintained on potato dextrose agar with a moistened sterile dacron swab. The spores and mycelia are then suspended in 10 milliliters of sterile potato dextrose broth and adjusted to 70 percent transmission at 660 nm.

Inocula for yeasts and bacterial strains are prepared from overnight broth cultures then diluted into potato dextrose agar to a final concentration of either 40 percent or 70 percent transmission at 660 nm.

When the organism is *Acholephasma laidlawii,* it is suspended in brain heart infusion broth supplemented with 2.5 percent yeast extract and 20 percent heat inactivated horse serum, and the broth adjusted to a final concentration of 60 percent transmission at 660 nm.

For three strains of *Candida albicans* and one strain of *Saccharomyces cerevisiae,* sterile saline is employed in place of potato dextrose broth. Assay plates are prepared by diluting the inoculum into appropriate molten agar medium, cooled to 45° C. to obtain a final concentration of 4 percent.

Seeded agar for *Bacillus subtilis* (two species) are prepared from a commercially available spore suspension which is diluted directly into molten agar (45° C.) to obtain a final concentration of 0.1 percent.

The seeded agar media thus prepared are dispensed into petri dishes for assays (11 milliliters per dish).

The samples to be tested for production of antifungal agent are applied to 6.2 mm. filter paper discs (25 microliter/disc) and air dried at 24° C. When the sample to be tested is crude broth, it may be centrifuged prior to application. The discs bearing the material to be tested are then applied employing sterile conditions to the seeded assay plates and the samples rewet with 25 percent sterile aqueous dimethylsulfoxide (25 $\mu$l/disc). The assay plates are then incubated at either 28° C. or 37° C. for 24 hours. In one of the assays for *Bacillus subtilis,* the sample is applied to a disc previously impregnated with 4M potassium chloride at 25 $\mu$l/disc and then air dried.

Following incubation, the inhibition zones are measured and recorded. The measurements are made from the extreme edge where growth differs from the background zone. The growths are noted as to appearance as fuzzy edge and clear center, hazy throughout, slightly hazy, very hazy or ringed.

The products of the present invention demonstrated a broad spectrum of antifungal activity in the foregoing tests.

In view of the broad spectrum of activity, the products of the present invention either singly or as a mixture are adaptable to being utilized in various applications of antifungal compositions. In such use, compounds may be admixed with a biologically inert carrier, generally with aid of a surface active dispersing agent, the nature of which would vary depending on whether the use is for the control of pathogens infecting man or animals, or for control of fungi in agriculture such as in soil or plant parts, or for the control of fungi in inanimate objects.

In compositions for medical applications, the compounds may be admixed with a pharmaceutically acceptable carrier, the nature of which will vary depending on whether the composition is to be topical, parenteral or oral.

If said application is to be topical, the drug may be formulated in conventional creams and ointments such as white petroleum, anhydrous lanolin, cetyl alcohol, cold cream, glyceryl monostearate, rose water and the like.

For parenteral applications, the compounds may be formulated in conventional parenteral solutions such as 0.85 percent sodium chloride or 5 percent dextrose in water, or other pharmaceutically acceptable compositions.

Compositions for oral administration may be prepared by intimately mixing the component drugs with any of the usual pharmaceutical media, including, for liquid preparations, liquid carriers such as water, glycols, oils, alcohols, and the like; and for solid preparations such as capsules and tablets, solid carriers such as starches, sugars, kaolin, ethyl cellulose, surface active dispersing agents, generally with lubricant such as calcium stearate, together with binders, disintegrating agents and the like.

These compositions are then administered in amounts sufficient to obtain the desired antifungal effect. For medical application, the method comprises administering to a subject in need of treatment a therapeutically effective antifungal amount of a compound of Formula I. The appropriate doses will vary depending on age, severity, body weight and other conditions. For topical application the compositions are applied directly to the area where control is desired. For internal administration, the composition may be applied by injection or may be administered orally.

For non medical application, the product of the present invention, either singly or as a mixture may be employed in compositions in an inert carrier which includes finely divided dry or liquid diluents, extenders, fillers, conditioners and excipients, including various clays, diatomaceous earth, talc, and the like, or water and various organic liquids such a lower alkanols, for example ethanol and isopropanol, or kerosene, benzene, toluene and other petroleum distillate fractions or mixtures thereof.

These compositions may be employed by applying to the surface of or incorporating in the medium to be protected. For the control of rice blast, tomato late blight, tomato early blight, wheat leaf rust, bean powdery mildew and tomato Fusarium wilt, the compositions may be applied directly to the plant in topical application or administered to the soil for systemic application. The method comprises administering to the affected plant, soil or medium to be protected are antifungally effective amount of the compound of Formula I.

The following examples illustrate the invention but are not to be construed as limiting.

Example I

Fermentation Production of Compound I-A

A frozen culture in glycerol, identified as MF 5038 WT and from a culture isolated from a soil sample and maintained in the Merck culture collection was employed in the fermentation. A 2 milliliter portion of the frozen culture was defrosted and aseptically transferred to a 250 milliliter unbaffled Erlenmeyer flask containing Medium 1. Medium 1, after inoculation, was incubated at 28° C. with rotary agitation (212 rpm, 2" throw shaker) for three days. At the end of this period, 2.0 milliliters of the growth were aseptically transferred to each of fourteen unbaffled 250 milliliter Erlenmeyer flask containing Medium 3. The inoculated Medium 3, was incubated at 25° C. for 14 days and thereafter employed in the isolation.

The media employed in the foregoing fermentation are:

| MEDIUM 1 (KF Seed Medium) | |
|---|---|
| Corn Steep Liquor | 5 g |
| Tomato Paste | 40 g |
| Oat Flour | 10 g |
| Glucose | 10 g |
| Trace Elements Mix | 10 ml |
| Distilled Water | 1000 ml |
| pH | 6.8 |
| Trace Elements Mix: | |
| $FeSO_4.7H_2O$ | 1 g |
| $MnSO_4.4H_2O$ | 1 g |
| $CuCl_2.2H_2O$ | 25 mg |
| $CaCl_2$ | 100 mg |
| $H_3BO_3$ | 56 mg |
| $(NH_4)_6MoO_2.4H_2O$ | 19 mg |
| $ZnSO_4.7H_2O$ | 200 mg |
| Distilled Water | 1000 ml |

| MEDIUM 2 | |
|---|---|
| Millet | 15 g per 250 ml flask |
| Liquid Supplement | 10 ml per 250 ml flask |
| Liquid Supplement: | |
| Ardamine pH | 0.2 g |
| $KH_2PO_4$ | 0.1 g |
| $MgSO_4.7H_2O$ | 0.1 g |
| Sodium tartrate | 0.1 g |
| $FeSO_4.7H_2O$ | 0.01 g |
| $ZnSO_4.7H_2O$ | 0.01 g |
| Distilled Water | 1000 ml |

MEDIUM 3

Medium 2 + 10 ml distilled water per 250 ml flask.

Ninety milliliters of methanol was added to fourteen flasks each containing about 40 milliliters of broth, partially as a solid cake, from the fermentation carried out in the manner above described. The solid was broken into smaller pieces and the contents transferred to a 2 liter flask. The resulting mixture was stirred for 1 hour, then filtered and the filtrate stored at 4° C. for four days. Some white crystalline precipitate formed. The precipitate was removed by filtration and the filtrate concentrated to 225 milliliters ("Concentrate").

Eighteen milliliters of the "Concentrate" was chromatographed on a ZORBAX ODS column (siliceous microparticulate particle porous for packed HPLC column from DuPont) (9.2 mm ID×25 cm) which had been equilibrated with 75:25 methanol/water by eluting with the same solvent mixture for twenty minutes at 4 milliters per minute. The bands eluting between 11 and 11.9 minutes were combined and concentrated to dryness and the residue dissolved in 1.5 milliliters of methanol. This sample was chromatographed on a silica gel plate ( GF Analtech Uniplate; 20 cm×20 cm, 2000 microns). The plate was developed with 9:1 methylene chloride/methanol. The band at the origin was recovered and eluted with methanol. The methanol eluate was concentrated to 0.5 milliliter, centrifuged, and the supernatant was separated. The solvent was evaporated therefrom to obtain a yellow oily residue weighing 3.4 milligrams.

A 1.5 milligram portion of this residue was employed in an antifungal assay and the remainder was employed for structural determination.

The assay was carried out in the manner previously described. The results showed activity against a number of fungal organisms with especially good activity against *Ustilago maydis.*

The structural determination was carried out employing mass spectral data and H NMR spectral data previously described and showed this product to be the compound having the structure IA.

Example II

Fermentation Production of Compound IA

Fifty milliliters of "Concentrate" in Example I was chromatographed on the ZORBAX column in a manner described in Example I. The column effluent eluting at 11.8 minutes was collected and concentrated to a residue weighing 17.7 milligrams.

Fifteen milligrams of the residue thus obtained was chromatographed on a preparative silica gel GF plate as described in Example I. The band at the origin was eluted with methanol and the methanol eluate dried to obtain a light yellow residue weighing 6.7 milligrams.

One milligram of the residue was employed in a limited fungal identification assay. Five milligrams of the residue was employed in a structure determination.

The fungal identification assay was carried out employing about 25 of the organisms. The product showed good activity against almost all of the organisms and especially against *Ustilago maydis;* five strains of *Candida albicans; Candida tropicalis; Aspergillus niger; Cryptococcus albidus;* and *Torulospora hansenii.*

This material was also shown by HRMS, $^{13}CNMR$ and $^1H$ NMR to be the compound of Formula IA.

Example III

Fermentation Production of Compound IB

In operations carried out in a manner similar to that described in Examples I, a slant of a preserved isolate of *Aspergillus fumigatus* MF 5038 was used to inoculate seed flasks containing 50 milliliters of KF seed medium. The inoculated flasks were incubated at 28° C. with agitation (220 rpm) for 48 hours. The seed growth (10 ml) was then used to inoculate media, each containing 0.5 liter of PBG medium in 2 liter flasks and the medium incubated at 25°-26° C. without agitation to produce the product in the mixture.

| MEDIUM 4 (PBG/Production Medium) | |
|---|---|
| Dextrose | 10 g |
| Ardamine pH | 5 g |
| Glycerol | 10 g |
| $(NH_4)_2SO_4$ | 2 g |
| Soybean Meal | 5 g |

-continued

| MEDIUM 4 (PBG/Production Medium) | |
|---|---|
| Tomato Paste | 5 g |
| Sodium Citrate | 2 g |
| Distilled Water | 1000 ml |
| pH 7.0, adjusted with 50% NaOH | |

One liter of methanol was added to each of the nine 2-liter flasks. Each flask contained an equivalent of approximately 320 milliliters of solid mycelial material. The mycelial solid material was broken into smaller pieces, the contents of all the flasks were pooled and the resulting mixture stirred for six hours. The mixture was then filtered and the filtrate concentrated to 800 milliliters.

The concentrate was charged on a 1 liter column of non ionic resin (Amberlite XAD-2 resin, Rohm and Haas Co.,) equilibrated in 0.2 percent aqueous ammonia. In a stepwise operation, first, 2 liters of 0.2 percent aqueous ammonia and then 2 liters of methanol were applied to the column and four 1 liter fractions were collected. Fraction 3 was concentrated to dryness and the residue stirred with 20 milliliters of methanol. The mixture was filtered and the filtrate charged on a 400 milliliter bed of Sephadex LH-20, (dextran gel filtrant, Pharmacia Fine Chemicals, Inc.) in methanol. The adsorbate was eluted with methanol. After collecting and discarding the first 200 milliliters of effluent, 20 milliliter fractions were collected, sampled and tested in the fungal assay. Fractions 7-10 which showed activity against *Ustilago maydis*, *Candida tropicalis* and *Candida albicans* were combined and concentrated to dryness. Nine milliliters of 9:1 methylene chloride/methanol was added to the residue, the resulting mixture filtered and the filtrate employed in the following chromatographic separation.

The filtrate was charged on a 250 gram column of silica gel and eluted sequentially with 1.5 liters of 9:1 methylene chloride/methanol (fractions 1-6), 1 liter of 1:1 methylene chloride/methanol, (fractions 7-10) 1 liter of methanol (fractions 11-14), and 1.5 liters of 1:1 methanol/water (fractions 15-18). Fractions 15 through 18 were combined, based on bioactivity, concentrated to dryness and the residue dissolved in 8 milliliters of 75:25 methanol/water. This sample was chromatographed in five portions on the ZORBAX column by eluting with the same solvent mixture at 4 milliliters per minute as described in Example I. The column effluent eluting at 11 minutes was concentrated to a residue weighing 5.7 milligrams. The material was employed in antifungal determinations.

The compound was found to be consistently active against most of the 41 of the filamentous fungi and yeasts of the antifungal assay previously described. The isolated material was identified by spectroscopic means to be Compound IB.

Example IV

Fermentation Production of Compound IB and IC

In operations carried out in a similar manner, a yeast malt extract slant section of *A. fumigatus* MF 5038 was inoculated into 54 milliliters of KF medium and incubated for 48 hours at 28° C. with agitation (220 rpm). The 1 milliliter portions of the multiple flasks each containing seed growth was then used to inoculate 40 milliliters of KF medium and the media incubated at 200 rpm for 24 hours. The entire contents of each such flask was used to inoculate 1.5 liters of sterilized PBG production medium contained in 20 liter jugs and the latter incubated at 26° C. for 12 days in a static liquid fermentation.

Thirty liters of broth from the above described liquid static fermentation was homogenized and stirred with 30 liters of ethyl acetate. The mixture was filtered to remove solid material and the filtrate of organic and aqueous liquids was separated.

The aqueous solution was charged on a 3 liter column of Amberlite XAD 2 resin in water, at a rate of 60 ml/min. Thereafter, the column was washed with 3 liters of deionized water, eluted with 6 liters of methanol, and six 1 liter fractions collected. Based on bioactivity, fractions 3, 4 and 5 were combined and concentrated under reduced pressure to 90 milliliters.

The material thus obtained was chromatographed on a column of Sephadex LH 20 resin (6 cm ID × 130 cm) and eluted with methanol at a rate of 10 ml/min. The first 600 milliliters of effluent were discarded and thereafter 20 milliliter cuts were retained. Cuts 22-50 were combined, concentrated to dryness under reduced pressure. The sample was chromatographed on a Magnum-20 Partisil 10/50 ODS 3 column. The column was eluted at 18 milliliters per minute with 75:25 methanol/water for 50 minutes. Fractions eluting between 19 and 23 minutes were combined and concentrated to 5 milliliters of aqueous solution. The sample was refrigerated to obtain white solids which were recovered by filtration and rinsed with 2 milliliters of ice cold water. The weight of the white solids was 214 milligrams.

The product subjected to HRMS and IH NMR was found to have the data previously described corresponding to Compound I-C.

In addition to the HRMS data and $^1$H NMR data, the following $^{13}$C NMR data was obtained.

The $^{13}$C NMR chemical shifts recorded in the manner previously described were as follows: 14.5, 21.3, 23.7, 26.77, 26.82, 29.9, 30.3, 30.6, 30.7, 33.1, 33.4, 38.42, 38.48, 61.1, 67.9, 72.5, 74.6, 77.9, 125.8, 138.9, 171.6 and 172.4 ppm.

Fractions which eluted from the Magnum 20 column between 15 and 18 minutes were combined and concentrated to dryness. The residue was dissolved in 10 milliliters of 75:25 methanol/water and chromatographed with recycling on the Magnum 20 column. Active fractions just prior to Compound I-C were combined and concentrated to a 5 milliliter aqueous solution. The solution was refrigerated (4° C.) for about 24 hours whereupon some white solid precipitated. It was recovered by filtration and it amounted to 3.0 milligrams. The product exhibited HRMS and $^1$H NMR properties previously described and characterized as that attributable to Compound I-B. In addition, $^{13}$C data was obtained which were as follows:

The $^{13}$C NMR chemical shifts recorded in CD$_3$OD at ambient temperature on Varian XL-400 NMR spectrometer given in ppm relative to tetramethylsilane at zero ppm using the solvent peak at 49.0 ppm as internal reference were as follows: 14.6, 23.7, 26.79, 26.82, 30.2, 30.4, 30.6, 30.7, 33.1, 33.5, 38.40, 38.46, 60.8, 69.3, 72.4, 75.2, 76.0, 130.2, 135.5, 171.9 ppm.

Example V

Fermentation Production of Compound ID

A 2.0 milliliter portion of the same frozen culture described in Example I (MF 5038 WT) was used to inoculate 10 agar slants of Medium 5,

| MEDIUM 5 | |
|---|---|
| Difco Potato Dextrose Agar | 39.0 g |
| Distilled Water | 1000 ml |

After incubation for 2-6 weeks at room temperature, a portion of one slant which showed green sporulation was used to inoculate a liquid fermentation medium (Medium 1). The inoculated medium was incubated at 28° C. with rotary agitation (212 rpm, 2" throw shaker) for 3 days. After 3 days of incubation, 2.0 milliliter portions of the growth were aseptically transferred to fifteen unbaffled 250 milliliter Erlenmeyer flasks containing Medium 3. The flasks containing inoculated Medium 3 were then incubated at 25° C. for 14 days. The fermentation broth thus obtained was employed in the isolation process.

Figure 1:
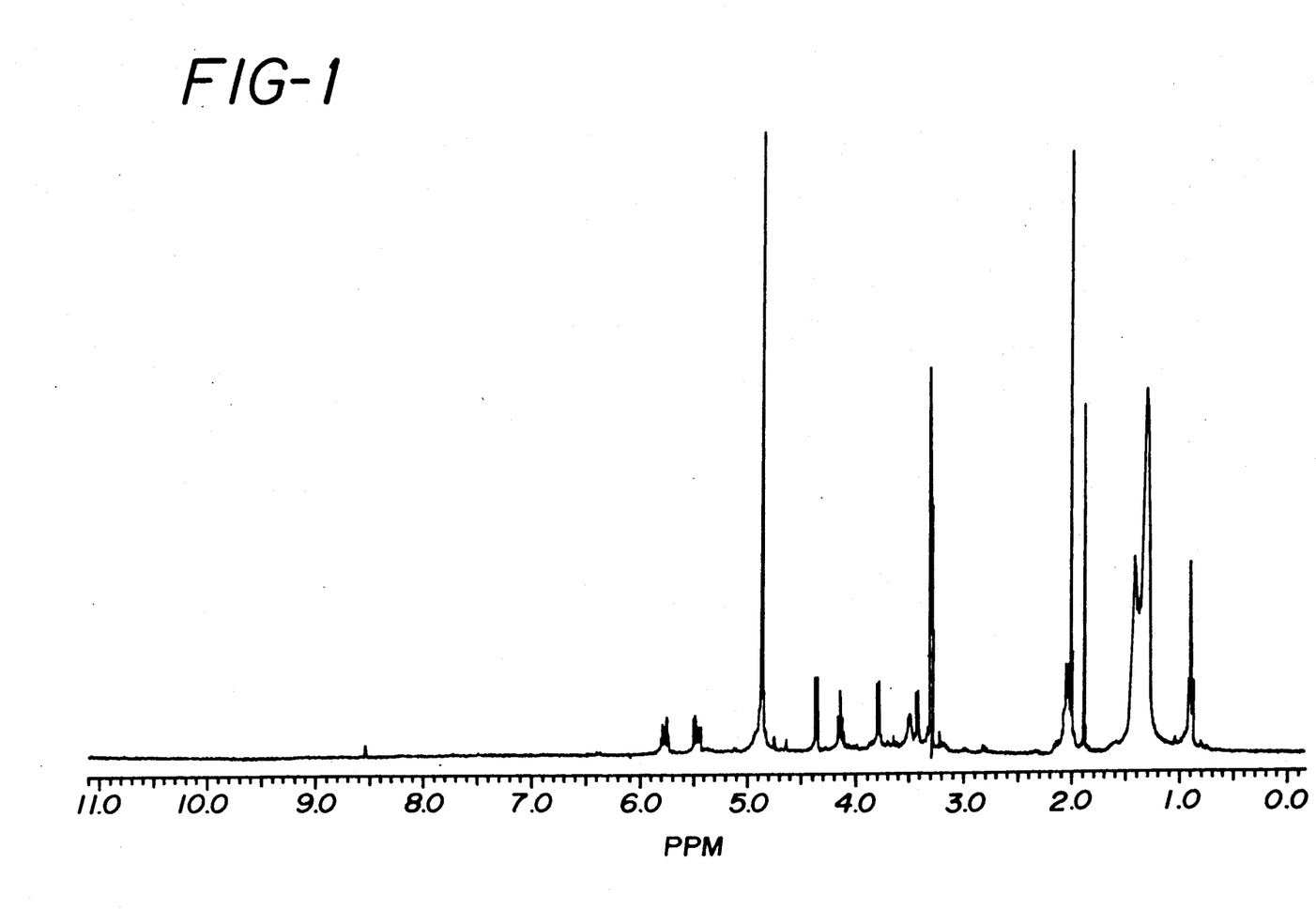
Figure 2:
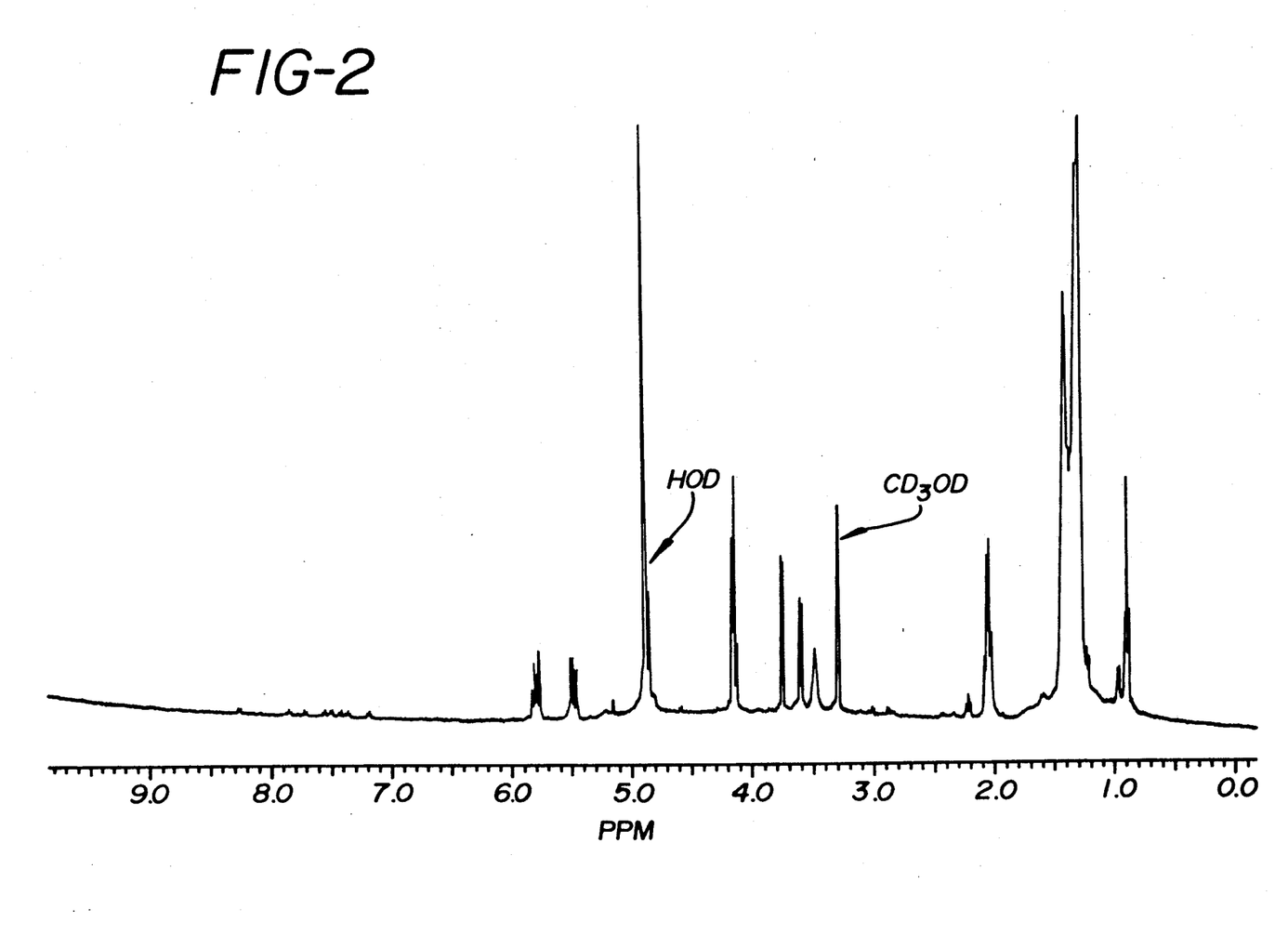
Figure 3:
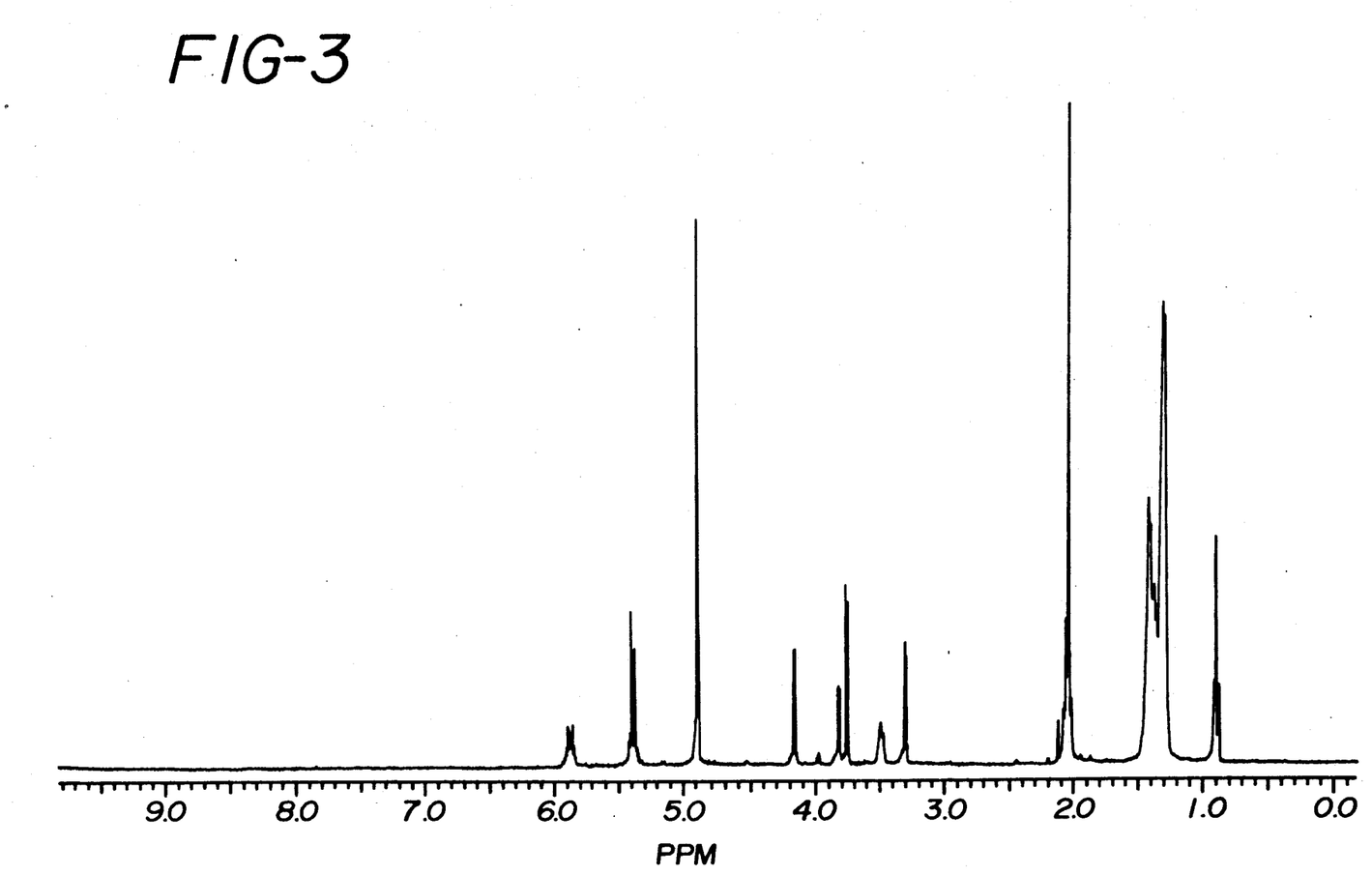
Figure 4:
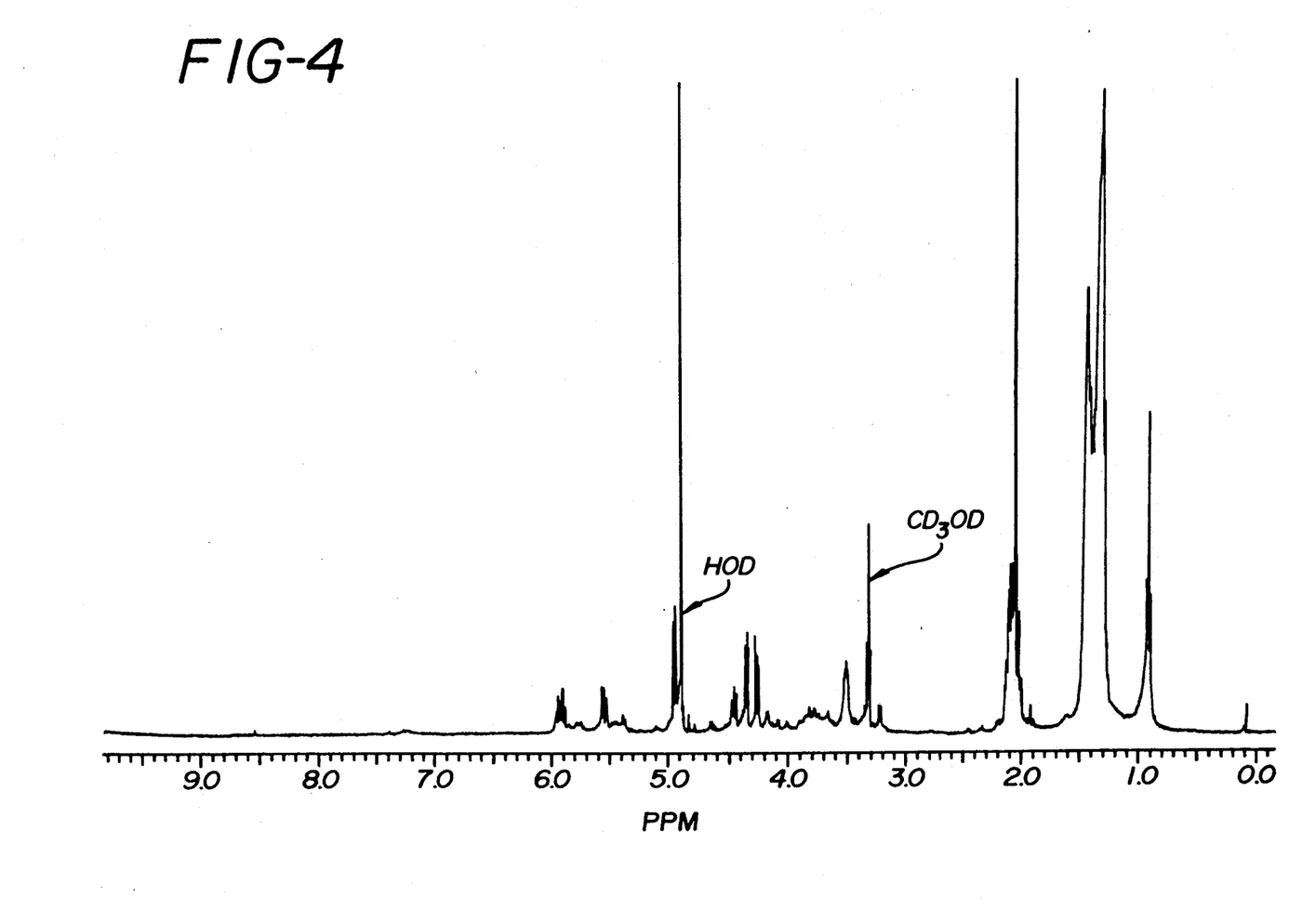

To these fifteen flasks, each containing 40 milliliters of the above described fermentation broth, was added 15 milliliters of deionized water and 40 milliliters of methanol. The contents of each flask was transferred to a 4-liter flask and 1:1 methanol/water added to bring the volume to 1.8 liters. The mixture was stirred for 2 hours and then filtered. This filtrate was retained, the solids were re extracted with 800 milliliters of 1:1 methanol/water, then filtered and the filtrate combined with the filtrate from the initial filtration. The combined filtrate was subjected to reduced pressure to evaporate the methanol and to obtain an aqueous solution which was freeze-dried. The residue was dissolved in 50 milliliters of ethyl acetate, stirred with 50 grams of silica gel Woelm, (activated silica gel, Woelm Pharma GM6H, W. Germany) dried, and slurried in methylene chloride. The sample was charged to a silica gel column and eluted stepwise with 500 milliliters each of methylene chloride; 1:1 methylene chloride/ethyl acetate; 1:1 ethyl acetate/ acetone; acetone; 3:1 and 1:1 acetone/methanol; and methanol. The 500 milliliter 1:1 acetone/methanol fraction was filtered and the filtrate concentrated to dryness. The residue was dissolved in 5 milliliters of methanol and chromatographed on a 350 milliliter column of Sephadex LH 20 using methanol and eluting solvent. Fractions were tested against *Ustilago maydis*. Those fractions active against the *Ustilago* organism were combined and chromatographed on a DuPont ZORBAX column in the manner described in Example 1. The effluents eluting between 13 and 19 minutes were combined and the solvent vaporized to obtain 3 milligrams of a yellow glassy residue. The compound was identified as Compound ID by mass spectral data previously described and $^1$H NMR Spectra (FIG. 4).

Example VI

Antifungal Activity in Agar Dilution Assay

In separate operations, in vitro antifungal activity determinations were carried out with Compound IB and with Compound IC against a panel of filamentous and yeast-like fungi employing yeast nitrogen base dextrose agar medium. In carrying out the assay, the compound to be tested was solubilized in 10 percent dimethyl sulfoxide (DMSO) supplemented with one drop of Tween 20. Two-fold dilutions were made with sterile distilled water/10% DMSO to obtain final concentrations in the agar dilution assay plates ranging from 64 to 0.06 µg/ml in the operation with Compound IB and from 128 to 0.06 µg/ml in the operation with Compound IC.

Nystatin (commercially available antifungal agent) was used as a positive antifungal control. The results are seen in the following table.

| Fungus | Strain No.* | Minimum Inhibitory Concentration (µg/ml) | | |
|---|---|---|---|---|
| | | Compound IC | Compound IB | Nystatin |
| *Cryptococcus neoformans* | MY1051 | 2 | 2 | 2 |
| *Cr. neoformans* | MY1146 | 2 | 2 | 2 |
| *Candida albicans* | MY1058 | 32 | 16 | 2 |
| *Ca. albicans* | MY1055 | 128 | 32 | 2 |
| *Ca. albicans* | MY0992 | 128 | 32 | 2 |
| *Ca. albicans* | MY1013 | 128 | 32 | 2 |
| *Ca. albicans* | MY1029 | >128 | 64 | 2 |
| *Ca. parapsilosis* | MY1009 | >128 | 32 | 4 |
| *Ca. parapsilosis* | MY1010 | 8 | 2 | 2 |
| *Ca. tropicalis* | MY1011 | 32 | 16 | 2 |
| *Ca. tropicalis* | MY1012 | 2 | 2 | >128 |
| *Ca. pseudotropicalis* | MY1040 | 2 | 0.5 | 1 |
| *Ca. krusei* | MY1020 | >128 | >64 | 2 |
| *Ca. rugosa* | MY1022 | >128 | >64 | 4 |
| *Ca. guilliermondi* | MY1019 | >128 | >64 | 2 |
| *Ca. stellatoidea* | MY1017 | 32 | 16 | 2 |
| *Torulopsis glabrata* | MY1059 | 16 | 16 | 1 |
| *Sac. cerevisiae* | MY1027 | 32 | 16 | 1 |
| *Aspergillus fumigatus* | MF4839 | 64 | 64 | 2 |
| *A. flavus* | MF0383 | 64 | 64 | 2 |
| *Pennicillium italicum* | MF2819 | 32 | >64 | 2 |

*Internal designation of strain

What is claimed is:
1. A compound of the formula where R is —H or —COCH₃, X is —OH, or —O⁻ and Y is —NH₂, —NH₃⁺, —NHCOCH₃ or provided that when R is —H and X is —OH, Y is —NHCOCH₃ or and when R is —H or —COCH₃ and X is —O⁻, Y is —NH₃⁺.

2. A compound of the formula or a mixture thereof.

3. A compound according to claim 2 which is the compound represented by Formula I-A.

4. A compound according to claim 2 which is the compound represented by Formula I-B.

5. A compound according to claim 2 which is the compound represented by Formula I-C.

6. A compound according to claim 2 which is the compound represented by Formula I-D.

7. A composition comprising a mixture of 2-amino-3,4,5,14-tetrahydroxy-6-eicosenoic acid, 5-acetoxy-2-amino-3,4,14-trihydroxy-6-eicosenoic acid, 2-acetylamino-3,4,5,14-tetrahydroxy-6-eicosenoic acid and 2-guanidino-3,4,5,14-tetrahydroxy-6-eicosenoic acid obtained by cultivating a microorganism of the genus *Aspergillus fumigatus* in a fermentation medium to obtain a mixture of compounds therein, separating the mixture from solid materials and thereafter isolating the products.

8. An antifungal composition which comprises one or more compounds of claim 1 and a biologically inert carrier.

9. A composition according to claim 8 in which the carrier is a pharmaceutically acceptable carrier.

10. A method for controlling fungi comprising administering an antifungally effective amount of one or more compounds of claim 1.

11. A method according to claim 10 in which the fungus is a pathogen and the amount administered is a therapeutically effective amount.

* * * * *